US012708539B2

(12) United States Patent
Murray, III et al.

(10) Patent No.: US 12,708,539 B2
(45) **Date of Patent: *Aug. 18, 2026**

(54) DELIVERY SYSTEM FOR DELIVERING AN ENDOVASCULAR GRAFT WITHIN A BLOOD VESSEL

(71) Applicant: Medtronic Vascular, Inc., Santa Rosa, CA (US)

(72) Inventors: Robert J. Murray, III, Santa Rosa, CA (US); Ross L. Wilcox, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/677,309

(22) Filed: May 29, 2024

(65) Prior Publication Data

US 2024/0407936 A1 Dec. 12, 2024

Related U.S. Application Data

(62) Division of application No. 17/388,227, filed on Jul. 29, 2021, now Pat. No. 12,023,267.

(51) Int. Cl.
*A61F 2/966* (2013.01)
*A61F 2/95* (2013.01)

(52) U.S. Cl.
CPC .......... *A61F 2/9661* (2020.05); *A61F 2/9517* (2020.05); *A61F 2002/9505* (2013.01); *A61F 2002/9665* (2013.01)

(58) Field of Classification Search
CPC .......... A61F 2/95; A61F 2/9517; A61F 2/962; A61F 2/966; A61F 2/9661; A61F 2/9662; A61F 2/243; A61F 2/2436; A61F 2/2439; A61F 2002/9505; A61F 2002/9511; A61F 2002/9665

See application file for complete search history.

(56) References Cited

U.S. PATENT DOCUMENTS 8,216,295 B2 7/2012 Benjamin et al.
8,414,640 B2 4/2013 Schmitt et al.
8,821,563 B2 9/2014 Orr et al.
9,364,359 B2 6/2016 Crawford et al.
2007/0233222 A1* 10/2007 Roeder .................. A61F 2/966 623/17.13
2011/0251666 A1* 10/2011 Schmitt ................ A61F 2/9661 623/1.11
2011/0301685 A1 12/2011 Kao (Continued)

*Primary Examiner* — Diane D Yabut

(74) *Attorney, Agent, or Firm* — Brooks Kushman P.C.

(57) ABSTRACT

A delivery system for delivering an endovascular graft within a blood vessel. The delivery system includes a tip assembly including a tip and a sleeve having an inner surface. The delivery system includes a tip capture mechanism. The tip assembly is configured to move axially relative to the tip capture mechanism and between a delivery position and a release position. The tip capture mechanism includes a cylindrical outer surface and knobs arranged around the cylindrical outer surface. Each knob has a pyramidal structure with a rounded apex. The knobs and inner surface of the sleeve are configured to cooperate to hold a portion of the endovascular graft when the tip capture mechanism and the tip assembly are in the delivery position.

14 Claims, 18 Drawing Sheets

(56) References Cited

U.S. PATENT DOCUMENTS

| | | | | |
|---|---|---|---|---|
| 2012/0150272 | A1* | 6/2012 | Melsheimer | A61F 2/966 623/1.11 |
| 2012/0296407 | A1* | 11/2012 | Caselnova | A61F 2/962 623/1.11 |
| 2013/0274860 | A1 | 10/2013 | Argentine | |
| 2019/0298557 | A1* | 10/2019 | Murray, III | A61F 2/2436 |

* cited by examiner

DELIVERY SYSTEM FOR DELIVERING AN ENDOVASCULAR GRAFT WITHIN A BLOOD VESSEL

CROSS-REFERENCE TO RELATED APPLICATIONS

This application is a divisional of U.S. application Ser. No. 17/388,227, filed Jul. 29, 2021, now U.S. Pat. No. 12,023,267 which issued on Jul. 2, 2024, the disclosure of which is incorporated in its entirety by reference herein.

TECHNICAL FIELD

The present disclosure relates generally to a delivery system for delivering an endovascular graft within a blood vessel (e.g., the aorta) and a method for delivering an endovascular graft within a blood vessel (e.g., the aorta).

BACKGROUND

Endovascular procedures are minimally invasive techniques to deliver a variety of clinical treatments in a patient's vasculature. One such clinical treatment that can be delivered through an endovascular procedure is a stent graft. A stent graft is an implantable device formed of a surgical graft covering and an expanding or self-expanding metal frame. The stent graft may be placed inside a blood vessel (e.g., the aorta) to bridge a diseased segment (e.g., an aneurismal segment or a dissected segment) of the blood vessel, thereby excluding or mitigating hemodynamic pressures of blood flow from the diseased segment of the blood vessel.

Endovascular grafts (e.g., stent grafts) may be deployed through a minimally invasive intraluminal delivery procedure. A lumen or vasculature may be accessed at a convenient and less traumatic entry point of the patient's body, and the endovascular graft may be routed through the vasculature to the site where the prosthesis is to be deployed. Intraluminal deployment typically uses a delivery catheter with tubes or shafts arranged for relative axial movement. For instance, an expandable stent graft may be compressed and disposed within a distal end of an outer shaft of the delivery catheter fixed to an inner shaft. The delivery catheter may then be maneuvered, typically tracked through a body lumen until a distal end of the delivery catheter and the stent graft are positioned at an intended treatment site. The expandable stent graft can then be deployed and radially expanded within the blood vessel.

SUMMARY

According to one embodiment, a delivery system for delivering an endovascular graft within a blood vessel is disclosed. The delivery system includes a tip assembly including a tip and a sleeve having an inner surface. The delivery system further includes a tip capture mechanism. The tip assembly is configured to move axially relative to the tip capture mechanism and between a delivery position and a release position. The tip capture mechanism includes a cylindrical outer surface and knobs arranged around the cylindrical outer surface. Each knob has a pyramidal structure with a rounded apex. The knobs and inner surface of the sleeve are configured to cooperate to hold a portion of the endovascular graft when the tip capture mechanism and the tip assembly are in the delivery position.

According to another embodiment, a method for delivering an endovascular graft within a blood vessel is disclosed. The method includes positioning delivery system having a tip assembly and a tip capture mechanism holding the endovascular graft in a radially compressed configuration at a deployment location with a blood vessel. The method further includes moving the tip assembly relative to the tip capture mechanism to release the endovascular graft into a release position to affix the endovascular graft into the blood vessel. The method also includes withdrawing the delivery system from the blood vessel without advancing the tip assembly and the tip capture mechanism beyond the deployment location. Alternatively, the method also includes withdrawing the delivery system from the blood vessel without moving the tip capture mechanism from the release position.

DETAILED DESCRIPTION

Figure 1A:
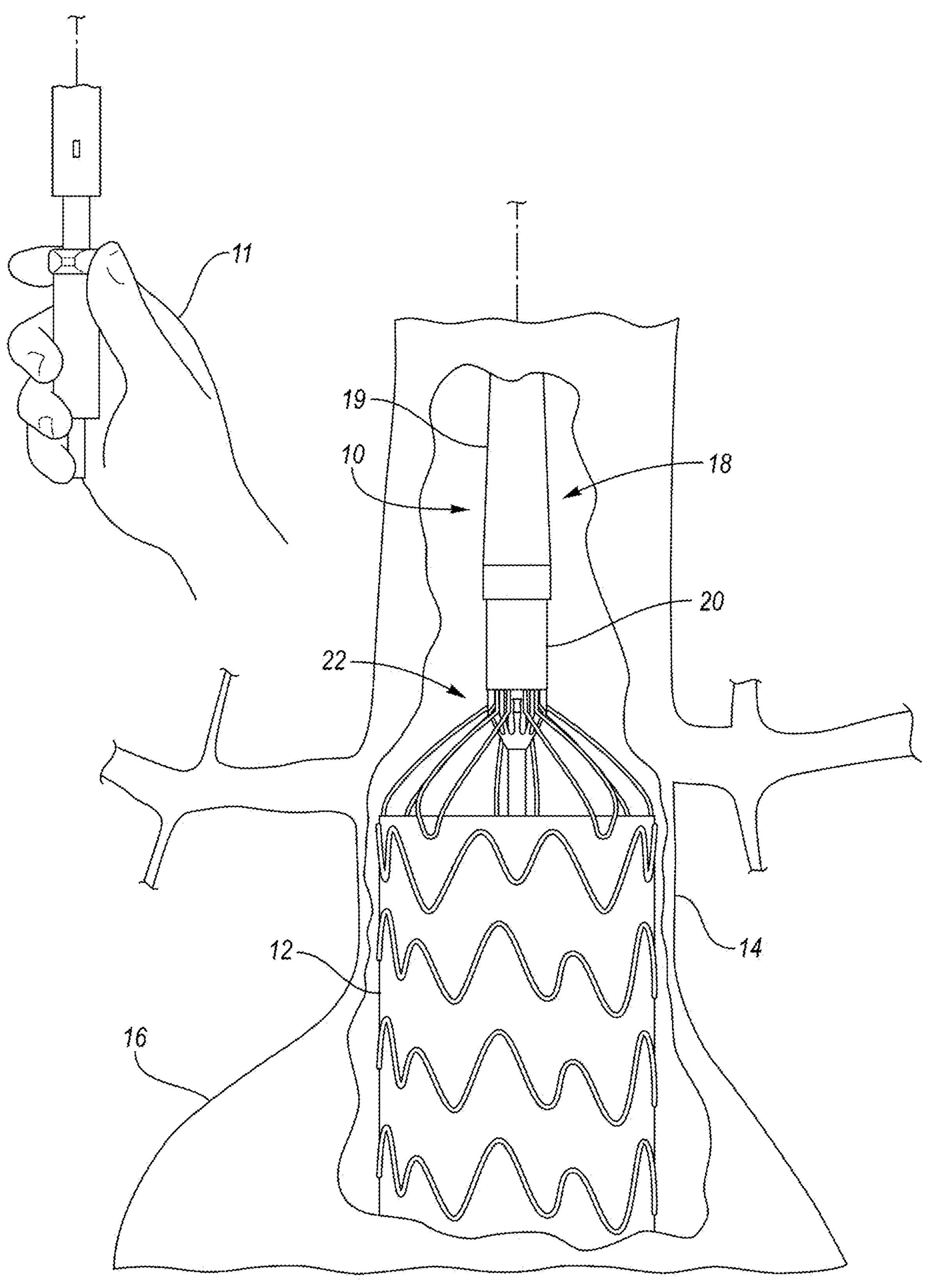
FIG. 1A is a side view of a delivery system during deployment of a stent graft within a blood vessel (e.g., aorta).

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Directional terms used herein are made with reference to the views and orientations shown in the exemplary figures. A central axis is shown in the figures and described below. Terms such as “outer” and “inner” are relative to the central axis. For example, an “outer” surface means that the surfaces faces away from the central axis, or is outboard of another “inner” surface. Terms such as “radial,” “diameter,” “circumference,” etc. also are relative to the central axis. The terms “front,” “rear,” “upper” and “lower” designate directions in the drawings to which reference is made.

Unless otherwise indicated, for the delivery system the terms “distal” and “proximal” are used in the following description with respect to a position or direction relative to a treating clinician. “Distal” and “distally” are positions distant from or in a direction away from the clinician, and “proximal” and “proximally” are positions near or in a direction toward the clinician. For the stent-graft prosthesis, “proximal” is the portion nearer the heart by way of blood flow path while “distal” is the portion of the stent-graft further from the heart by way of blood flow path.

The following detailed description is merely exemplary in nature and is not intended to limit the invention or the application and uses of the invention. Although the description is in the context of treatment of blood vessels such as the aorta, coronary, carotid, and renal arteries, the invention may also be used in any other body passageways where it is deemed useful.

Endovascular stent grafting, or endovascular aneurysm repair (EVAR), is a form of treatment for abdominal or thoracic aortic aneurysm that is less invasive than open surgery. Endovascular stent grafting uses an endovascular stent graft to reinforce the wall of the aorta and to help keep the damaged area from rupturing by isolating the aneurysm from blood flow. Stent grafts are typically tubular open-ended structures providing support for damaged, collapsing, or occluded blood vessels, such as the aorta. Stent grafts are flexible, which allows them to be inserted through, and conform to, tortuous pathways in the blood vessels. For example, stent grafts may be radially expandable from a radially compressed configuration for delivery to the affected vessel site to a radially expanded configuration when deployed at the affected vessel treatment site. The radially expanded configuration has a larger diameter than the radially compressed configuration. Stent grafts may be inserted in the radially compressed configuration and expanded to the radially expanded configuration either through a self-expanding mechanism, or using a balloon catheter, for example.

In one example, an EVAR procedure may include inserting a guide wire into a portion of the patient’s body, such as the femoral artery. Once the guidewire is inserted into the artery, it may be gently pushed toward the site of the aneurysm. A stent graft delivery system, which may include a catheter and stent graft, may be placed over the guidewire, and inserted along the guidewire into the site of the aneurysm. The stent graft may be guided within the catheter in its radially compressed configuration to the site of the aneurysm. Radiopaque markers may be located at a distal end of the stent graft delivery system or on the stent graft itself to permit a surgical technician to guide the stent graft into a proper position. Once in the proper position, the stent graft can be expanded from the radially compressed configuration to the radially expanded configuration. This can be done, for example, by pulling back a stent-graft cover, allowing the stent graft to expand due to its fabric being biased outwards. Once deployed into the radially expanded configuration, the stent graft can be held in place with metallic hooks or stents. The catheter can then be removed, while the stent graft remains.

Figure 1B:
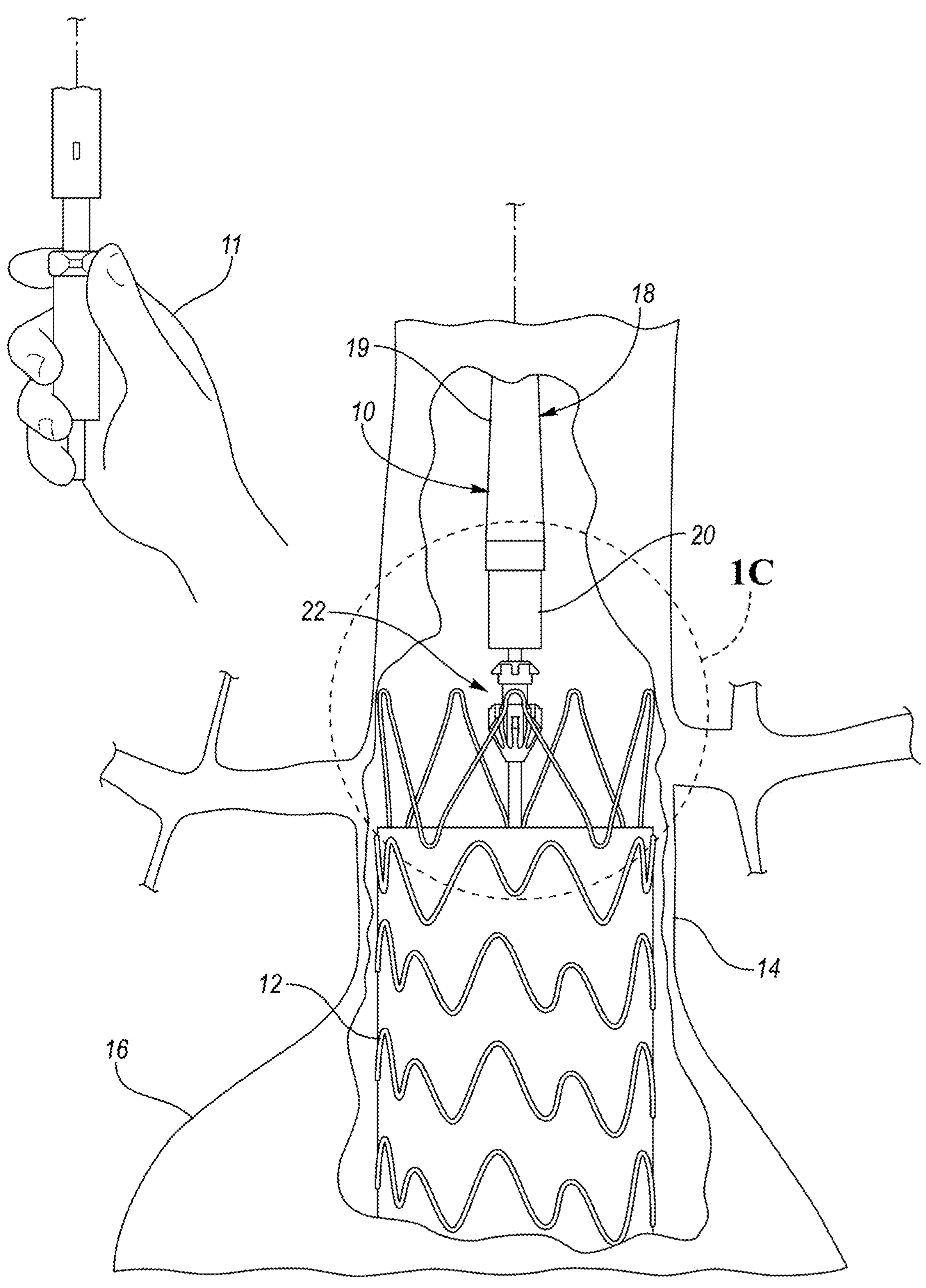
FIG. 1B is a side view of the stent graft released from the delivery system.

FIG. 1A shows delivery system 10 being guided by surgical technician 11 during deployment of stent graft 12 within blood vessel 14. As shown in FIG. 1A, blood vessel 14 is the aorta, and more particularly the abdominal aorta. FIG. 1B shows delivery system 10 released from stent graft 12 and stent graft 12 affixed within blood vessel 14. Once affixed within blood vessel 14, stent graft 12 is configured to provide a conduit for blood flow through stent graft 12. As shown in FIGS. 1A and 1B, stent graft 12 is located within an aneurysm 16 of blood vessel 14. Blood flowing through stent graft 12 may reduce pressure within aneurysm 16, thereby reducing or stabilizing the size of aneurysm 16. Graft material of stent graft 12 may be a non-permeable material, such as polyester terephthalate (PET), expanded polyester terephthalate (ePET), polytetrafluoroethylene (PTFE), polyurethane, or silicone. Blood or other fluid is prevented from passing through the non-permeable graft material. The graft material may also be formed of a natural material such as pericardium or another membranous tissue such as intestinal submucosa. The stent of stent graft 12 may be formed of a radially compressible and expandable material configured to self-expand into apposition with the interior wall of blood vessel 14. The stent may be coupled to the graft material to support the graft material. The stent may be constructed of stainless steel, a pseudo-elastic metal such as a nickel titanium alloy or nitinol, various polymers, or a super alloy having a base metal of nickel, cobalt, chromium, or other metal. The stent may be formed of a sinusoidal patterned ring including a number of crowns or bends and a number of struts or straight segments with crowns being formed between pairs of opposing struts.

Delivery system 10 includes tip assembly 18 and tip capture mechanism 22 (e.g., a spindle). Tip assembly 18 includes tip 19 and sleeve 20. Tip 19 may have a tapered profile. Tip 19 is configured to provide a leading edge to delivery system 10 and to track over one or more guidewires of delivery system 10. Sleeve 20 extends from tip 19 and defines an internal cavity configured to contain at least a portion of tip capture mechanism 22 during one or more steps of deploying stent graft 12 within blood vessel 14. For instance, tip capture mechanism 22 is at least partially contained within sleeve 20 during the step shown in FIG. 1A. Sleeve 20 is configured to conceal sharp features (e.g., protrusions) of tip capture mechanism 22 by containing those features within sleeve 20.

Figure 1C:
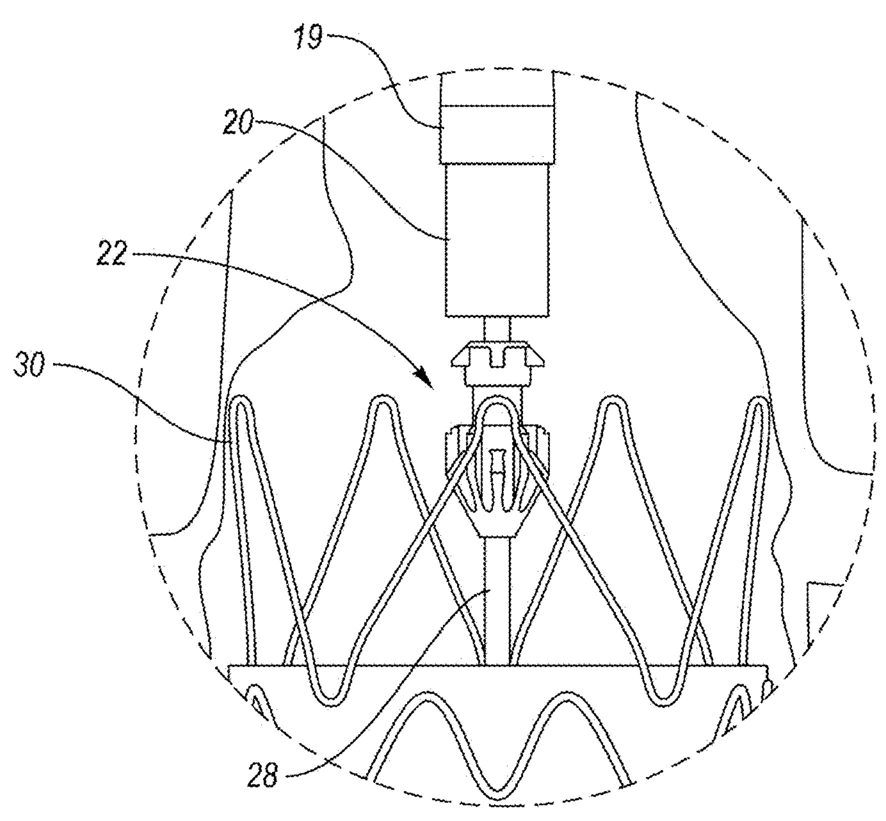
FIG. 1C is a magnified, side view depicting a tip assembly and a tip capture mechanism of the delivery system.
Figure 1D:
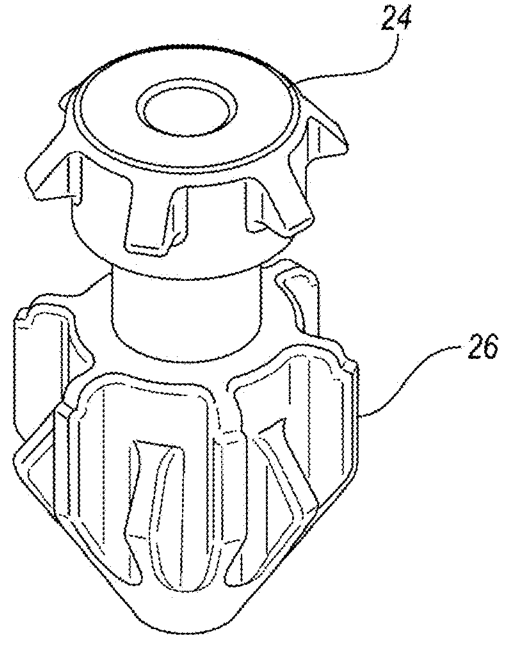
FIG. 1D is a magnified, isolated view of the tip capture mechanism including a fin assembly and a post coupled to the fin assembly.

As shown in FIG. 1D, tip capture mechanism 22 includes post 24 and fin assembly 26. Post 24 and fin assembly 26 of tip capture mechanism 22 and sleeve 20 are configured to cooperate to hold a structure (e.g., stent, ring, or loop) at a proximal end of stent graft 12 in a radially compressed configuration. In this configuration, the structure of the proximal end is disposed between sleeve 20 and tip capture mechanism 22. Tip capture mechanism 22 is fixed to lumen 28. Once stent graft 12 in its radially compressed configuration is in a proper position within blood vessel 14, tip assembly 18 may be translated axially away from surgical technician 11 relative to a guidewire lumen, thereby removing the structure of the proximal end of stent graft 12 from sleeve 20. Exposing the proximal end structure of stent graft 12 releases the proximal end structure of stent graft 12 from post 24 and fin assembly 26 of tip capture mechanism 22 to release stent graft 12 from delivery system 10 as shown in FIG. 1B. FIG. 1B depicts stent graft 12 in a radially expanded configuration.

Figure 1E:
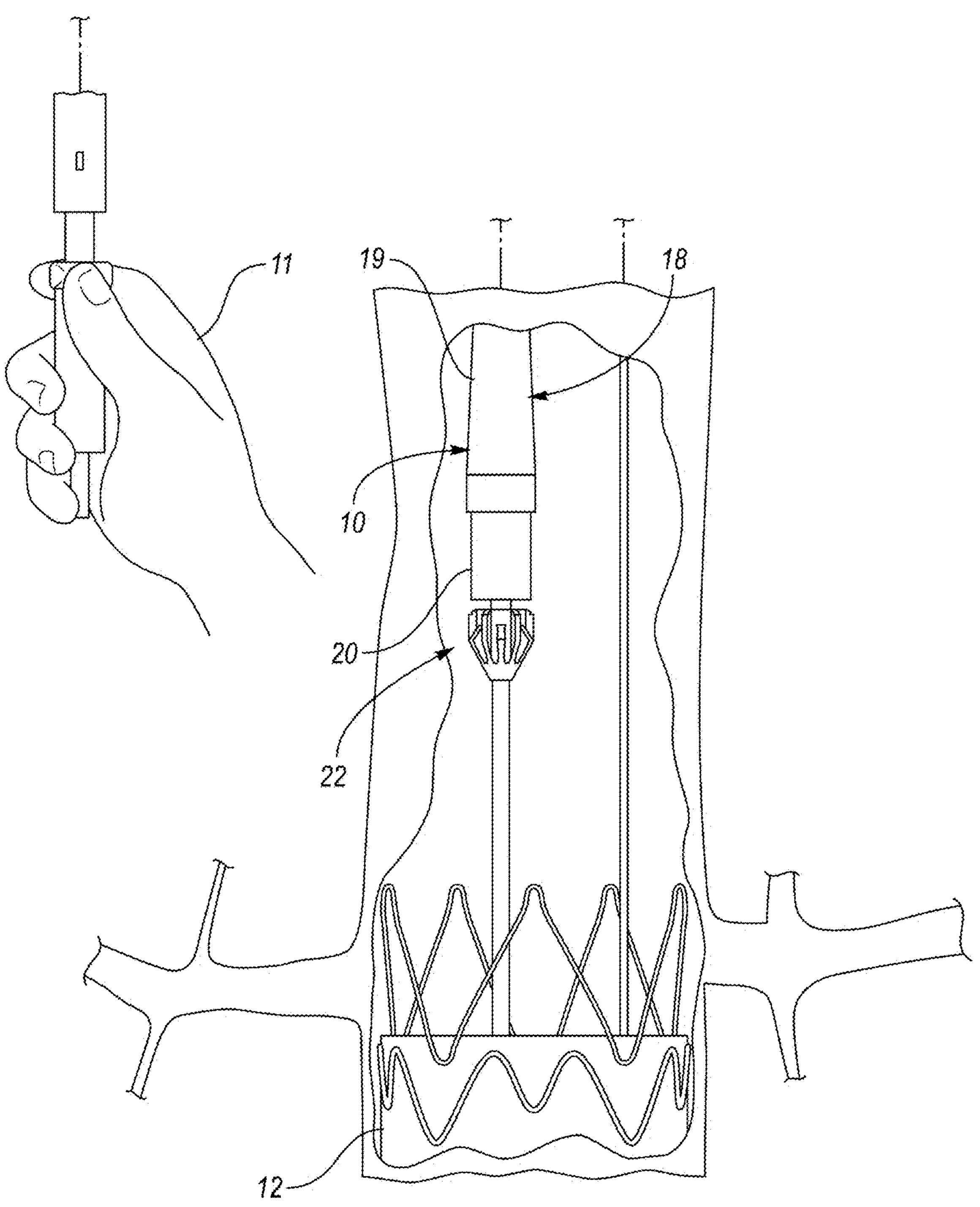
FIG. 1E is a side view of the delivery system in an advanced position after being released from the stent graft and advanced away from the stent graft and a surgical technician.

As shown in FIG. 1C, stent graft 12 has been released from delivery system 10. Once stent graft 12 is released from delivery system 10, tip capture mechanism 22 is exposed to the anatomy of blood vessel 14. The sharp features (e.g. protrusions) included on post 24 and fin assembly 26 may complicate removal of delivery system 10 from blood vessel 14. In severe cases, these sharp features may displace stent graft 12 from its proper position within blood vessel 14. Post-deployment steps may be utilized to reduce the risk of the complications. These post-deployment steps may include re-mating or recapturing tip capture mechanism 22 including post 24 and fin assembly 26 within sleeve 20 of delivery system 10. As shown in FIG. 1E, delivery system 10 is advanced up the anatomy of blood vessel 14 so that tip capture mechanism 22 and tip assembly 18 clear supra renal stent 30 on stent graft 12. Thereafter, sleeve 20 of tip assembly 18 is remated or recaptured with tip capture mechanism 22, thereby concealing post 24 and fin assembly 26 of tip capture mechanism 22 from the anatomy of blood vessel 14, thereby reducing the likelihood that sharp features of post 24 or fin assembly 26 catch on stent graft 12 or supra renal stent 30 during removal of delivery system 10. While these additional steps reduce risk of the tip capture mechanism catching on stent graft 12 or supra renal stent 30, these steps may lengthen and complicate the procedure using delivery system 10, thereby potentially increasing the total radiation exposure to the patient and the surgical technician.

Figure 2:
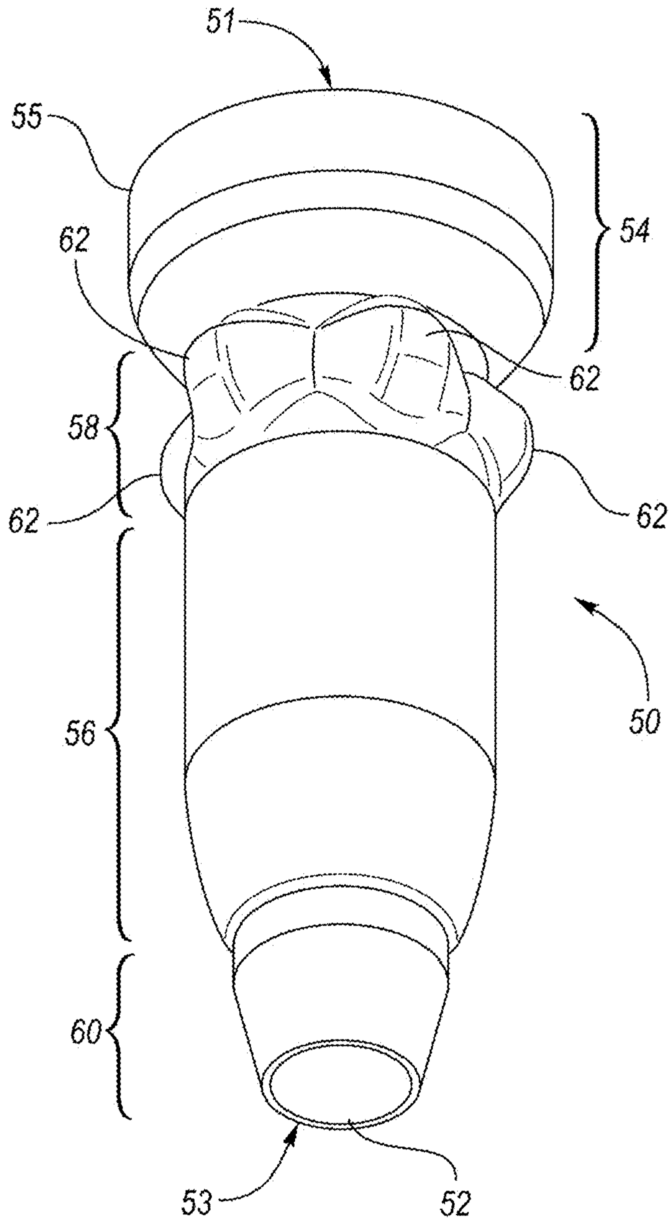
FIG. 2 is a perspective, side view of a tip capture mechanism for use in a delivery system according to one embodiment.
Figure 3A:
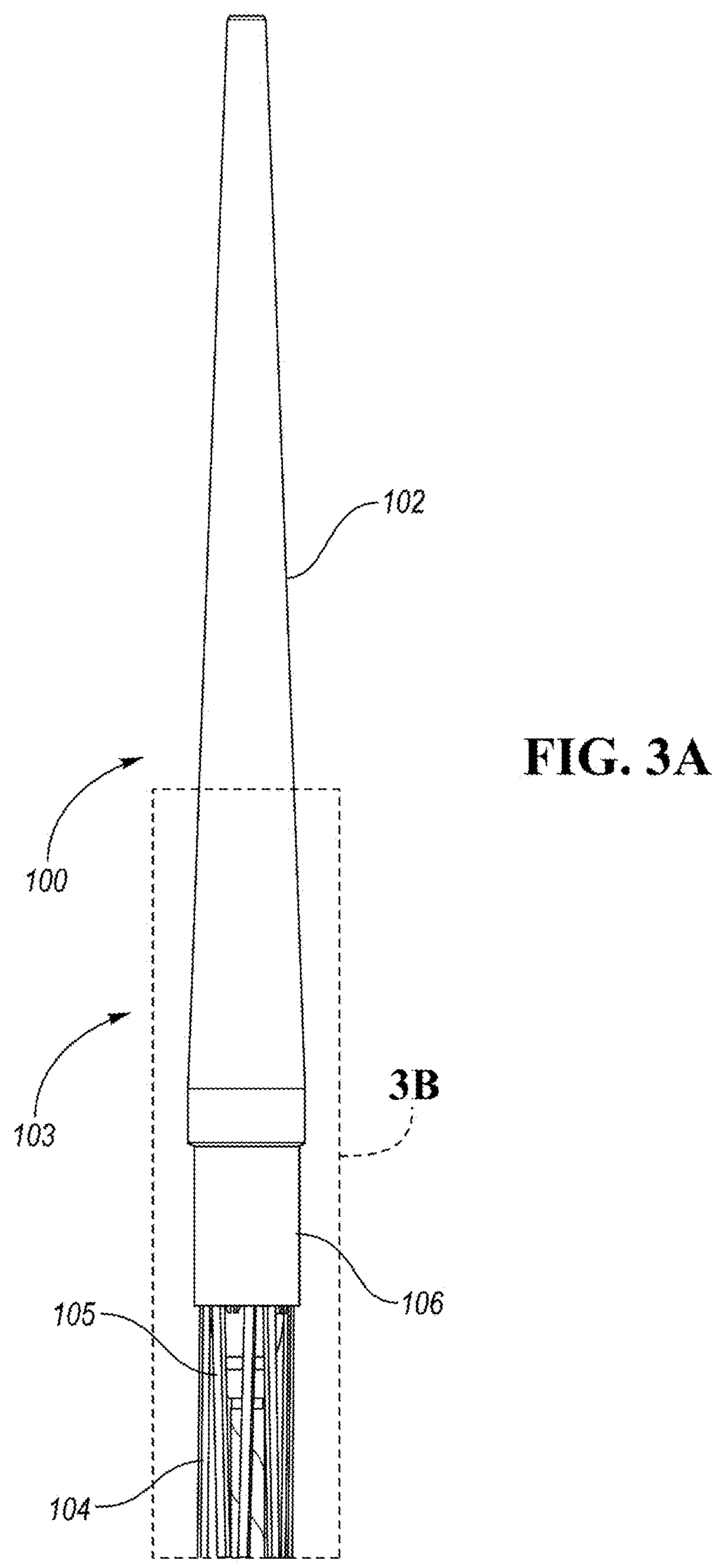
FIG. 3A is a side view of a delivery system including the tip capture mechanism of FIG. 2 where the delivery system is in a delivery position.
Figures 3B, 3C:
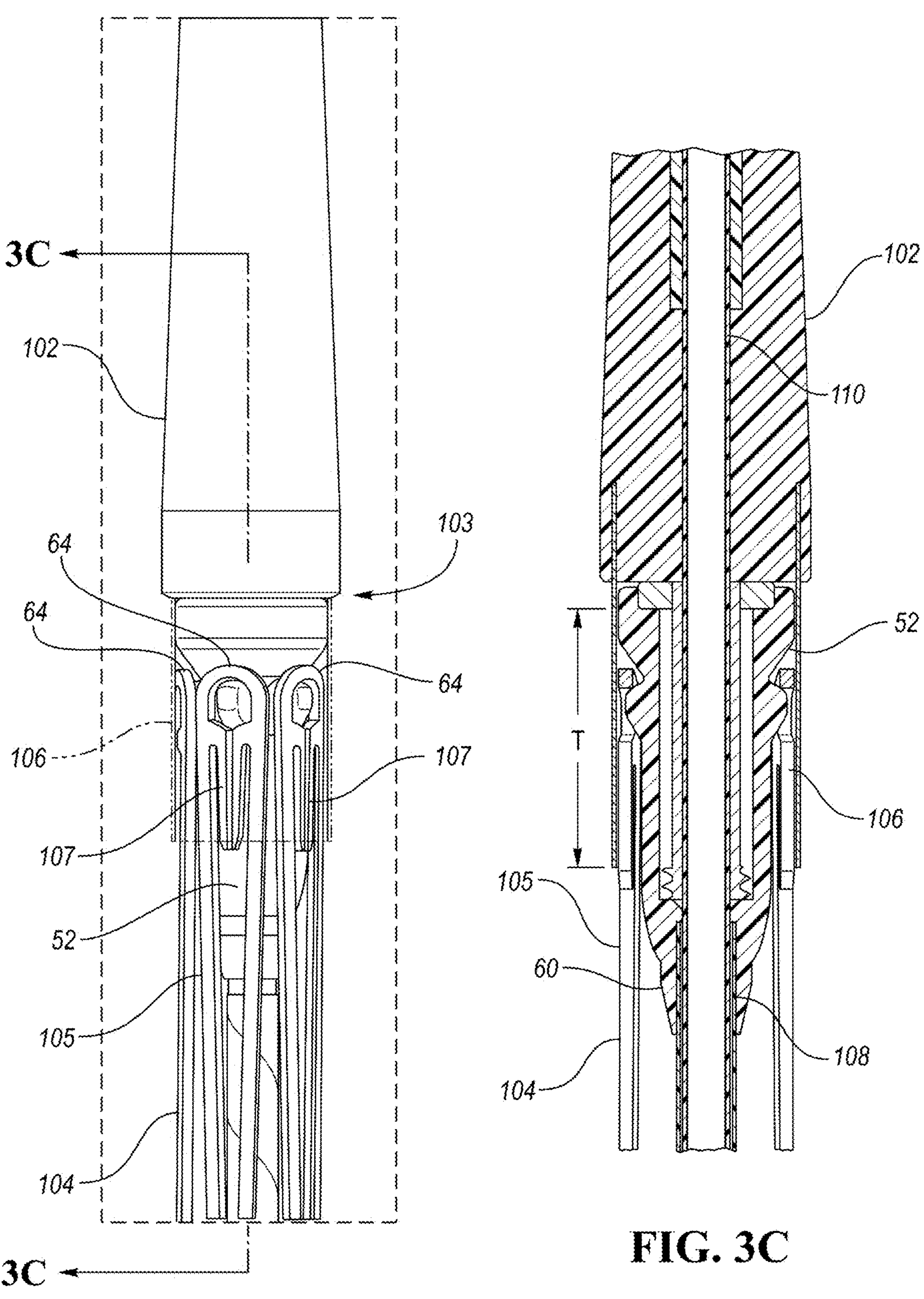
FIG. 3B is a side view of the delivery system of FIG. 3A with the sleeve of the delivery system depicted in phantom lines to show the attachment of the stent graft to the tip capture mechanism.
FIG. 3C is a cross-sectional view taken along line 3C-3C of FIG. 3B.

FIG. 2 depicts tip capture mechanism 50 in delivery system 100 as shown in FIG. 3B according to one embodiment that addresses one or more of the drawbacks identified herein with respect to the use of tip capture mechanism 22. The tip capture mechanism may also be referred to as a tip capture spindle or simply a spindle. Tip capture mechanism 50 is formed of a generally cylindrical shape defining tip capture mechanism channel 52 configured to receive a guidewire lumen. Tip capture mechanism 50 may include an elongated cylindrical outer surface extending along a longitudinal axis of tip capture mechanism 50. Tip capture mechanism 50 includes distal end 51 and proximal end 53 proximal tip assembly 103 with tip capture mechanism channel 52 extending therebetween. Tip capture mechanism 50 may be integrally formed or formed from two or more components coupled to one another to form tip capture mechanism 50. Tip capture mechanism 50 may be formed of any suitable material, including, without limitation, steel, stainless steel, polycarbonate or polyether ether ketone (PEEK) using machining or molding methods.

As shown in FIG. 2, tip capture mechanism 50 includes distal cylindrical portion 54 proximal to tip 102 of tip assembly 103 of delivery system 100 as shown in FIGS. 3B, central cylindrical portion 56, engagement portion 58 situated between distal cylindrical portion 54 and central cylindrical portion 56, and proximal conical portion 60 extending away from central cylindrical portion 56. In the embodiment shown in FIG. 2, central cylindrical portion 56 and proximal conical portion 60 do not include any fins. Central cylindrical portion 56 includes a regular cylindrical surface extending into regular frustoconical sections toward proximal conical portion 60. In one or more embodiments, regular refers to a surface not including any bumps, ridges, or uneven parts. As shown in FIG. 2, proximal conical portion 60 includes a regular frustoconical section. Distal cylindrical portion 54 includes a main cylindrical portion with first and second rounded edges, and further includes a conical section extending between the second rounded edge and engagement portion 58. The features of distal cylindrical portion 54 may be regular to reduce the possibility of distal cylindrical portion 54 catching on stent graft 104 and anatomy while removing delivery system 100 from the patient. Distal cylindrical portion 54 may include landing zone 55 configured to land proximal end 112 of sleeve 106 as described, for example, below. Central cylindrical portion 56 includes a main cylindrical portion extending into a series of reduced diameter conical sections. The features of central cylindrical portion 56 may be regular to reduce the possibility of central cylindrical portion 56 catching on stent graft 104 and anatomy while removing delivery system 100 from a patient. Distal cylindrical portion 54 may include a distal end portion with a distal end portion diameter. Proximal conical portion 60 may include a proximal end portion with a proximal end portion diameter. In one embodiment, the distal end portion diameter is greater than the proximal end portion diameter.

As shown in FIG. 2, engagement portion 58 includes circumferentially spaced knobs or protrusions, including knobs 62. Engagement portion 58 may include 6 knobs, although a different number of knobs, such as 4, 5, 7, 8, 9, or 10, may be implemented to accommodate the design of the supra renal stent 30. The circumferentially spaced knobs may be equally spaced around engagement member 58 (e.g., around a circular portion of the elongated cylindrical outer surface normal to the longitudinal axis of tip capture mechanism 50). In other embodiments, the circumferentially spaced knobs may be unequally spaced around engagement member 58. The knobs may have a generally pyramidal shape with rounded lateral edges, a rounded apex, and rounded base edges. These rounded features are configured to reduce the possibility of engagement portion 58 catching on stent graft 104 and anatomy while removing delivery system 100 from a patient. Each knob may have the same shape. In other embodiments, the shape of each knob may differ. One or more of the knobs may include only smooth features. As used in one or more embodiments, a smooth feature only has angles that are less than 45 degrees (and in some embodiments 40 degrees or 35 degrees).

FIGS. 3A through 3C depict deliver system 100 including tip capture mechanism 50 capturing stent graft 104 in a radially compressed configuration. As shown in this embodiment, only regular features of tip capture mechanism 50

(e.g., proximal conical portion 60 and a portion of central cylindrical portion 56) are exposed beyond sleeve 106. Knobs 62 of engagement portion 58 and sleeve 106 are configured to cooperate to hold loops or apices 64 of stent graft 104 at a proximal end of stent graft 104 in a radially compressed configuration. Anchor pins 107 extend away from loops and are configured to anchor stent graft 104 to the inner surface of blood vessel 14. Anchor pins 107 are concealed by sleeve 106 so that the anchor pins are unlikely to catch improperly on the anatomy of the patient. FIGS. 3A through 3C show supra renal stent 105 of stent graft 104. In the radially compressed configuration, the structure of the proximal end is disposed between sleeve 106 and tip capture mechanism 50. Tip capture mechanism 50 is fixed to lumen 108 at proximal conical portion 60 of tip capture mechanism 50. Delivery system 100 includes guidewire lumen 110. Once stent graft 104 in its radially compressed configuration and is in a proper position within blood vessel 14, tip assembly 103 may be translated axially away from surgical technician 11 relative to guidewire lumen 110, thereby removing the structure of the proximal end of stent graft 104 from sleeve 106. Exposing the proximal end structure of stent graft 104 releases the proximal end structure of stent graft 104 from knobs 62 of engagement portion 58 to release stent graft 104 from delivery system 100, thereby changing stent graft 104 from the radially compressed configuration to the radially expanded configuration.

Figure 4A:
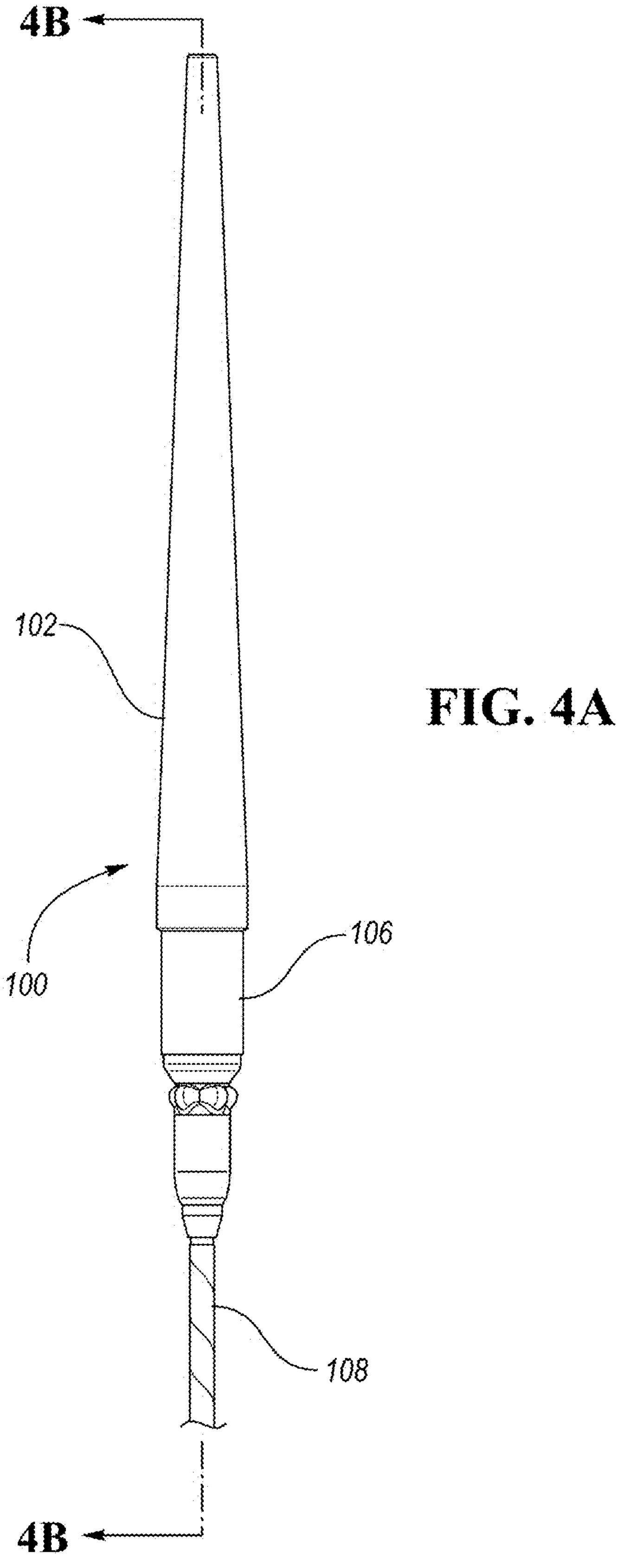
FIG. 4A is a side view of the delivery system of FIG. 3A where the delivery system is in a release position.
Figures 4B, 4C:
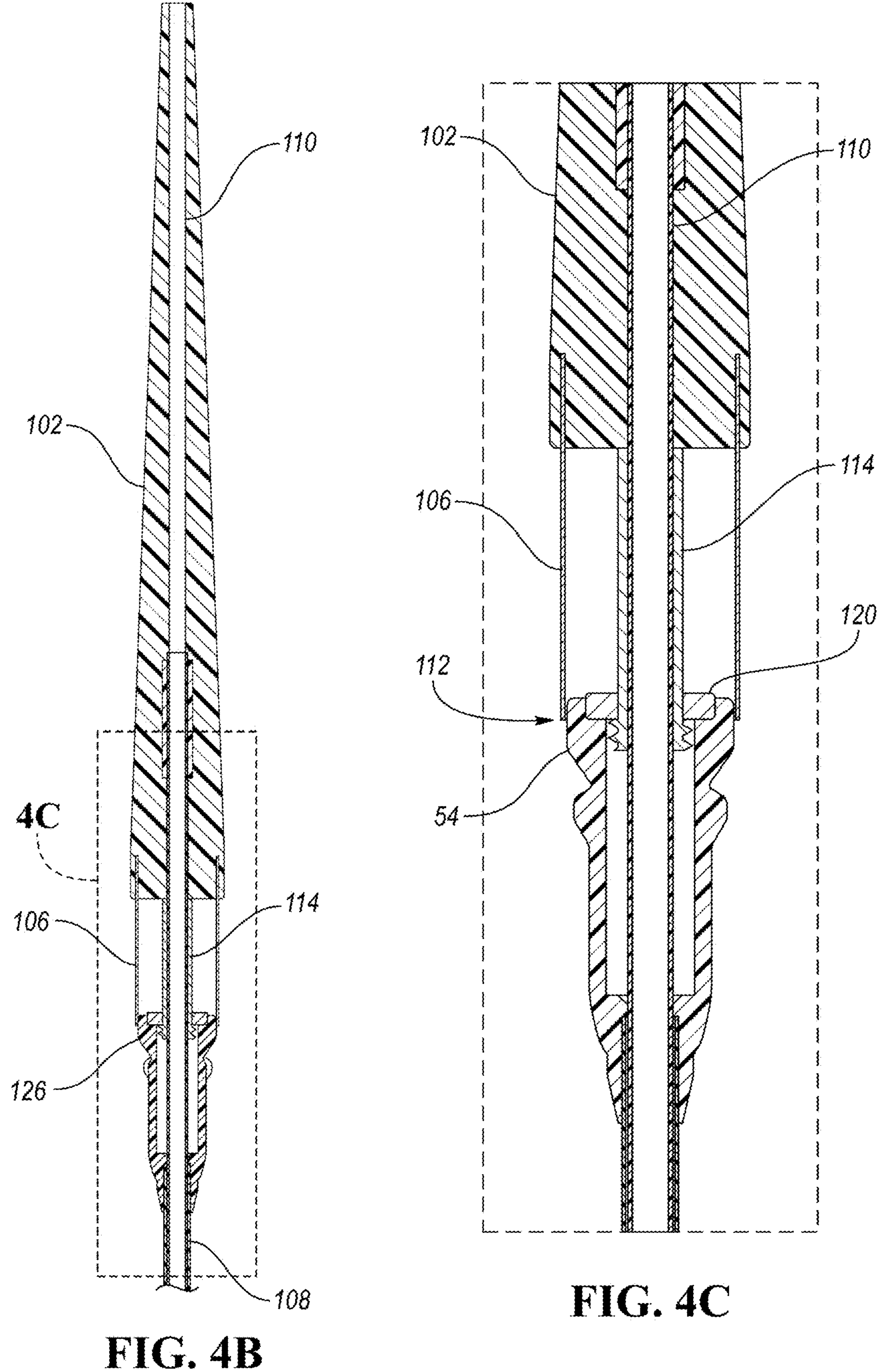
FIG. 4B is a cross-sectional view taken along line 4B-4B of FIG. 4A.
FIG. 4C is a magnified, cross-sectional view of FIG. 4B.
Figures 5A, 5B:
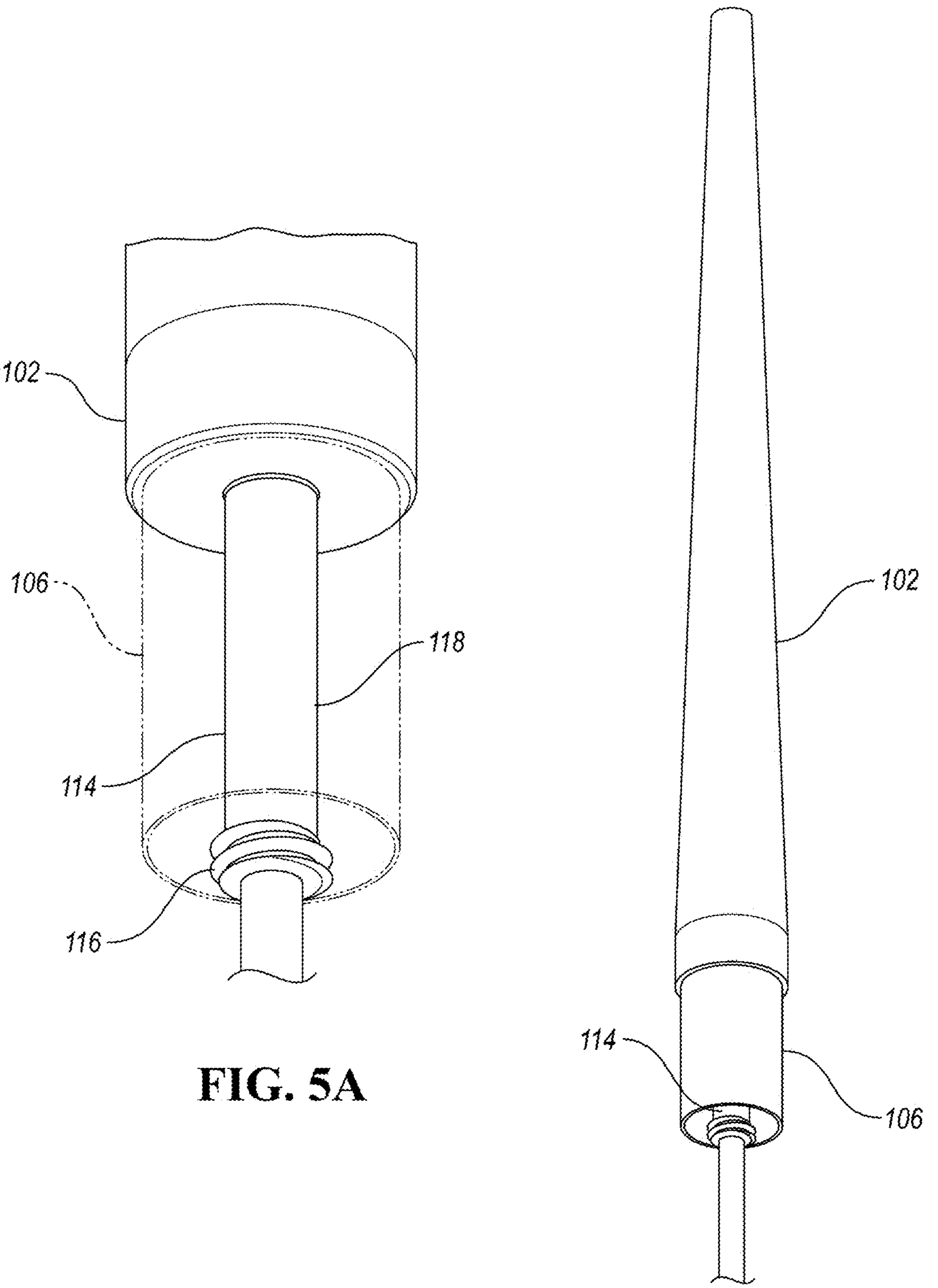
FIG. 5A is an isolated, perspective view of sleeve and travel limiter of the delivery system of FIG. 3A.
FIG. 5B is an isolated, perspective view of sleeve and travel limiter of the delivery system of FIG. 3A.

FIGS. 4A through 4C shows delivery system 100 in a release position after being released from stent graft 104. In the advanced position, proximal end 112 of sleeve 106 contacts a landing zone 55 of distal cylindrical portion 54. The travel distance between the delivery position shown in FIGS. 4A through 4C and the advanced position shown in FIGS. 5A through 5C is depicted by travel distance T shown in FIG. 3C. The landing zone 55 and distal cylindrical portion 54 have regular features with an overall profile of delivery system 100 remaining smooth and edgeless as possible during withdrawal of delivery system 100, thereby reducing or minimizing any impact of the sharp features of proximal end 112, which otherwise tends to catch on features of stent graft 104 during removal of delivery system 100. Once delivery system 100 is in the release position, tip assembly 103 (including sleeve 106) has an atraumatic design allowing delivery system 100 to be removed without a recapturing step (e.g., recapturing tip capture mechanism 22 in tip assembly 18). One or more procedural steps may be removed by eliminating the recapturing step, thereby reducing time, radiation exposure and/or possible complications.

As shown in FIGS. 4B and 4C and FIGS. 5A and 5B, delivery system 100 includes travel limiter 114 configured to maintain the position of tip assembly 103 and tip capture mechanism 50 relative to each other in the release position and during removal of delivery system 100. Travel limiter 114 includes elongated shaft 118 and screw threads 116 at a proximal end of elongated shaft 118. Travel limiter 114 is coupled to tip 102. Travel limiter 114 is configured for axial movement away from surgical technician 11 along guidewire lumen 110 from the delivery position shown in FIGS. 3A through 3C to the release position shown in FIGS. 4A through 4C. Delivery system 100 includes end plate 120 defining an aperture having aperture threads. The end plate 120 may be a separate component, as shown, or it may be integrally formed with the tip capture mechanism 50. If it is a separate component, it may be press-fit or otherwise secured within the channel 52 (e.g., by adhesive). Aperture threads and screw threads 116 are configured to move relative to each other to permit travel limiter 114 to enter tip capture mechanism channel 52. Before deployment, screw threads 116 of travel limiter 114 are threaded through aperture threading of end plate 120 such that travel limiter 114 is moved into and contained within tip capture mechanism channel 52. The diameter of tip capture mechanism channel 52 may be larger than the diameter of screw threads 116 to permit axial movement of travel limiter 114 within tip capture mechanism channel 52. Once through end plate 120, travel limiter 114 is configured to further move in an axial direction within tip capture mechanism channel 52. During deployment, tip 102 and travel limiter 114, which are coupled to each other, are free to move in an advance direction until screw threads 116 contact end plate 120. Travel limiter 114 is configured to not exit end plate 120 unless rotated. Such rotation may occur during assembly and before deployment. In one embodiment, about 2 full rotations may remove tip assembly 103 from tip capture mechanism 50. The lumen in tip 102 may be coupled to the back end of delivery system 10 to minimize rotation of tip 102 after assembly to reduce or minimize risk that tip 102 would unthread and exit tip capture mechanism 50. During assembly of delivery system 100, tip 102 may be loaded over tip capture mechanism 50 and stent graft 104 but can also be simply removed by unscrewing screw threads 116 of travel limiter 114, thereby providing a reversible design.

After the tip 102 has been coupled to the travel limiter 114 and before advancement of tip 102 to release the stent graft 104, the screw threads 116 may be disposed in a first, proximal position within the tip capture mechanism channel 52 (e.g., as shown in FIG. 3C). When the delivery system is in the desired position to release the stent graft 104, the physician or operator may advance the tip 102 in a distal direction. As the tip 102 is advanced, the travel limiter 114 and screw threads 116 may advance, as well. When a certain advancement distance has been reached, the screw threads 116 may contact the end plate 120, preventing further advancement (e.g., as shown in FIG. 4C). The travel distance between the proximal position to the distal (stopped) position may be configured to be at least long enough for the tip 102 to allow the release of the proximal stent of the stent graft 104, thereby allowing the stent graft to self-expand and deploy from the delivery system. As shown in FIG. 4C, in the final position, the tip 102 and tip capture mechanism 50 may form a continuous outer surface or contour with no gaps therebetween. The continuous outer surface or contour may be free from any sharp or jagged edges that may snag the stent graft or the vessel wall during withdrawal of the delivery system. Accordingly, no recapture step may be necessary, and the delivery system may be withdrawn immediately after deployment of the stent graft.

Figure 6A:
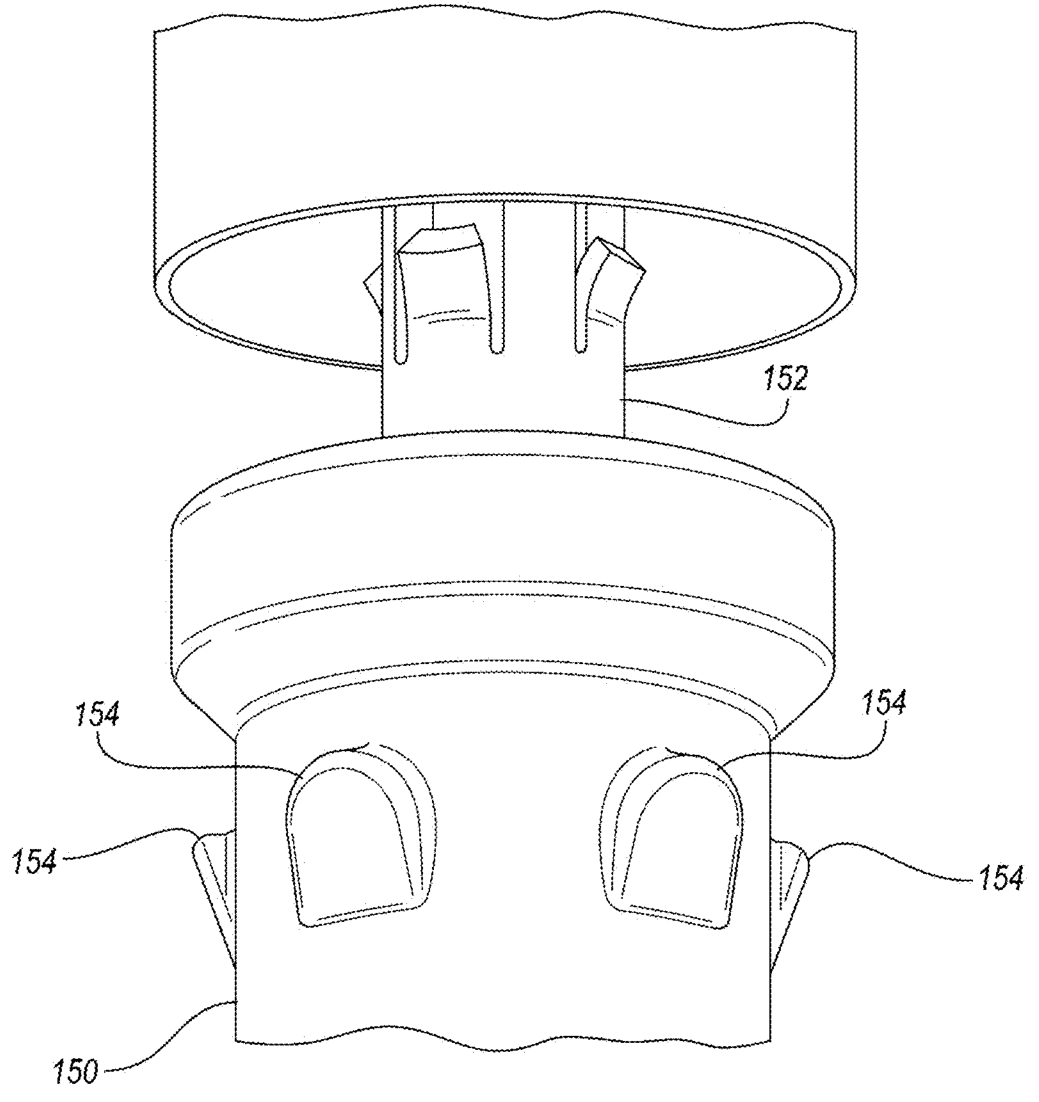
FIG. 6A is a perspective view of a delivery system according to a second embodiment.
Figure 6B:
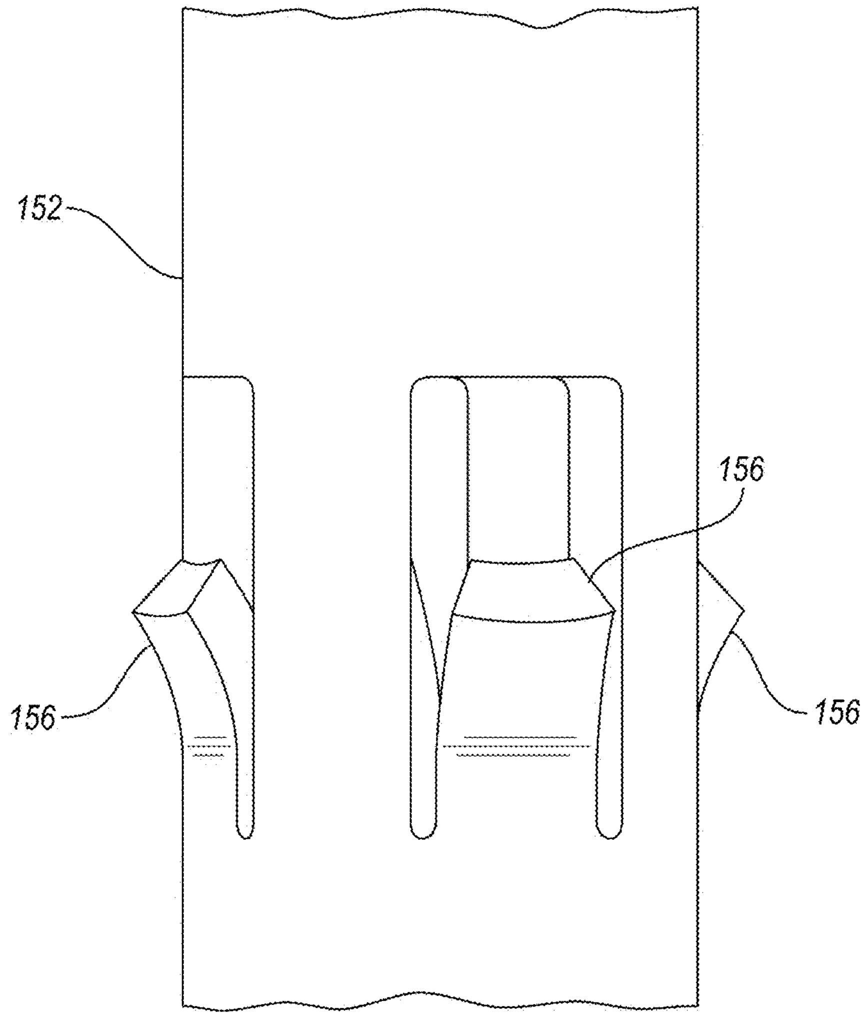
FIG. 6B is a side view of a travel limiter of the delivery system of FIG. 6A.

FIGS. 6A and 6B depict tip capture mechanism 150 and travel limiter 152 of delivery system 151 according to a second embodiment. Tip capture mechanism 150 includes ramps 154 with cylindrical upper surfaces configured to hold loops, apices, or other structures of a stent graft at a proximal end of the stent graft in a radially compressed configuration. Tip capture mechanism 150 may include 6 ramps, although a different number of ramps, such as 4, 5, 7, 8, 9 or 10, may be implemented to match the design of the supra renal stent 30. The ramps may be equally spaced around tip capture mechanism 150. In other embodiments, the ramps may be unequally spaced around tip capture mechanism 150. While tip capture mechanism 50 and tip capture mechanism 150 are shown with knobs 62 and ramps 154, respectively, knobs or ramps may be used in either embodiment.

Travel limiter 152 includes outwardly flared tabs 156. Travel limiter may include 4 tabs, although a different number of tabs may be equally spaced around travel limiter 152. Travel limiter 152 may be formed of an elastic or resilient material, for example, a super elastic memory metal, such as NiTi. Outwardly flared tabs 156 of travel limiter 152 may be formed from a laser cut super elastic memory metal material tube. Outwardly flared tabs 156 of travel limiter 152 are bent outward but have enough flexibility to bend inward as travel limiter 152 is inserted into tip capture mechanism 150. Once inserted, the tabs bend outwardly, thereby preventing travel limiter 152 from exiting tip capture mechanism 150.

Figures 7A, 7B:
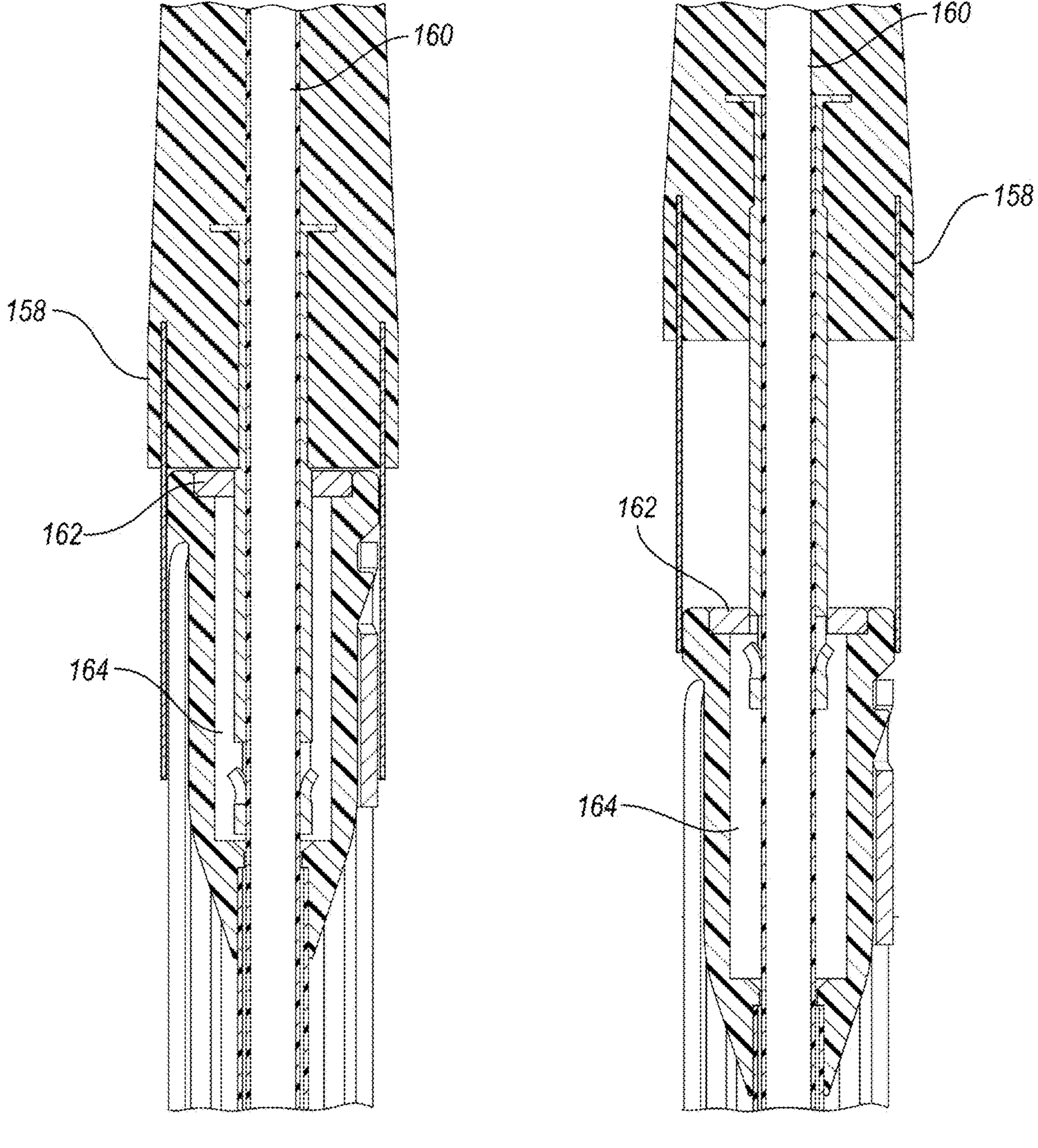
FIG. 7A is a fragmented, cross-sectional view including the delivery system of FIG. 6A in a delivery position.
FIG. 7B is a fragmented, cross-sectional view including the delivery system of FIG. 6A in a release position.

As shown in FIGS. 7A and 7B, travel limiter 152 is coupled to tip 158. Travel limiter 152 is configured for axial movement away from surgical technician 11 along guidewire lumen 160 from the delivery position shown in FIG. 7A to the release position shown in FIG. 7B. Delivery system 151 includes end plate 162. Similar to end plate 120, end plate 162 may be a separate component or integrally formed in the tip capture mechanism 150. During assembly, the tabs of travel limiter 152 are bent inward as travel limiter 152 is inserted into tip capture mechanism 150 such that travel limiter 152 is contained within tip capture mechanism channel 164. The diameter of tip capture mechanism channel 164 may be larger than the diameter of travel limiter 152 including outwardly flared tabs 156 to permit axial movement within tip capture mechanism channel 164. Once through end plate 162, travel limiter 152 is configured to move in an axial direction. During deployment, tip 158 and travel limiter 152, which are coupled to each other, are free to move in an advanced direction until tabs 156 contact end plate 162, thereby preventing further axial travel so that travel limiter 152 is not pulled out of the tip capture mechanism 150 after release.

In an alternative embodiment, handle assembly 200 shown in FIGS. 8A through 8C and FIGS. 9A and 9B is configured to move tip assembly 103 a travel distance T of FIG. 3C from the delivery position shown in FIGS. 4A through 4C to the advanced position shown in FIGS. 5A through 5C. Handle assembly 200 may be used instead of travel limiter 114. Handle assembly 200 includes rear handle 202 and rear grip 204 provided for grip by a surgical technician. Handle system 200 also includes back end thread 206 of screw gear 208, back end T-tube 210, thumb wheel 212 and inner member 214.

Figure 8A:
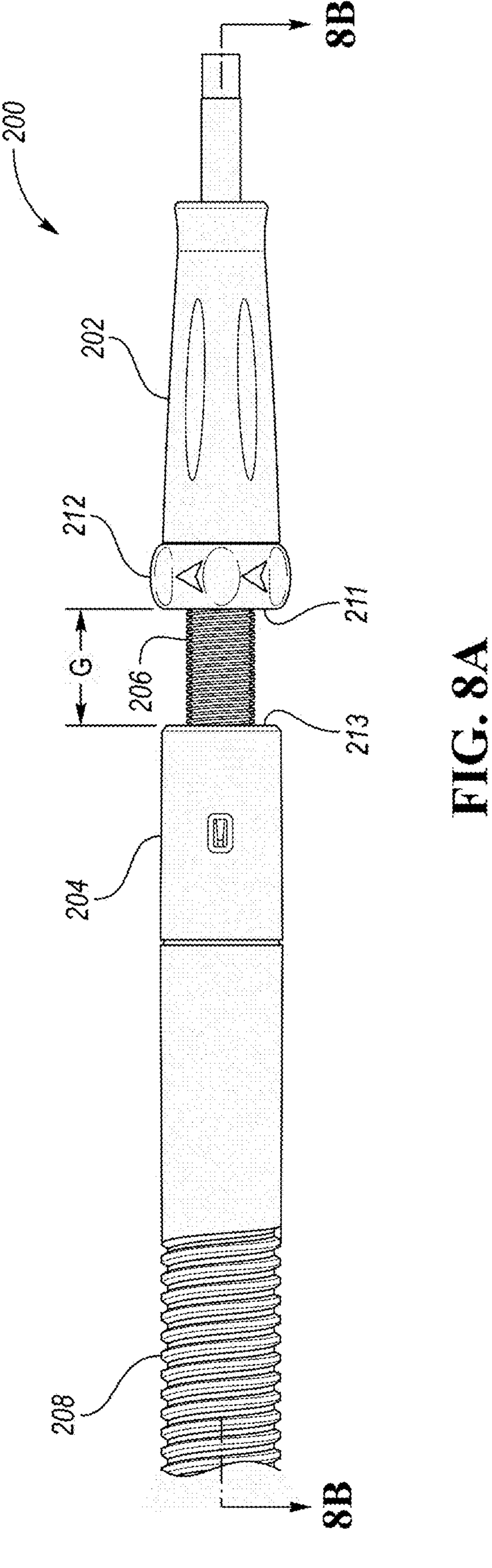
FIG. 8A is a fragmented, side view of a handle assembly of a delivery system where the handle assembly includes a tip assembly positioning mechanism.
Figure 8B:
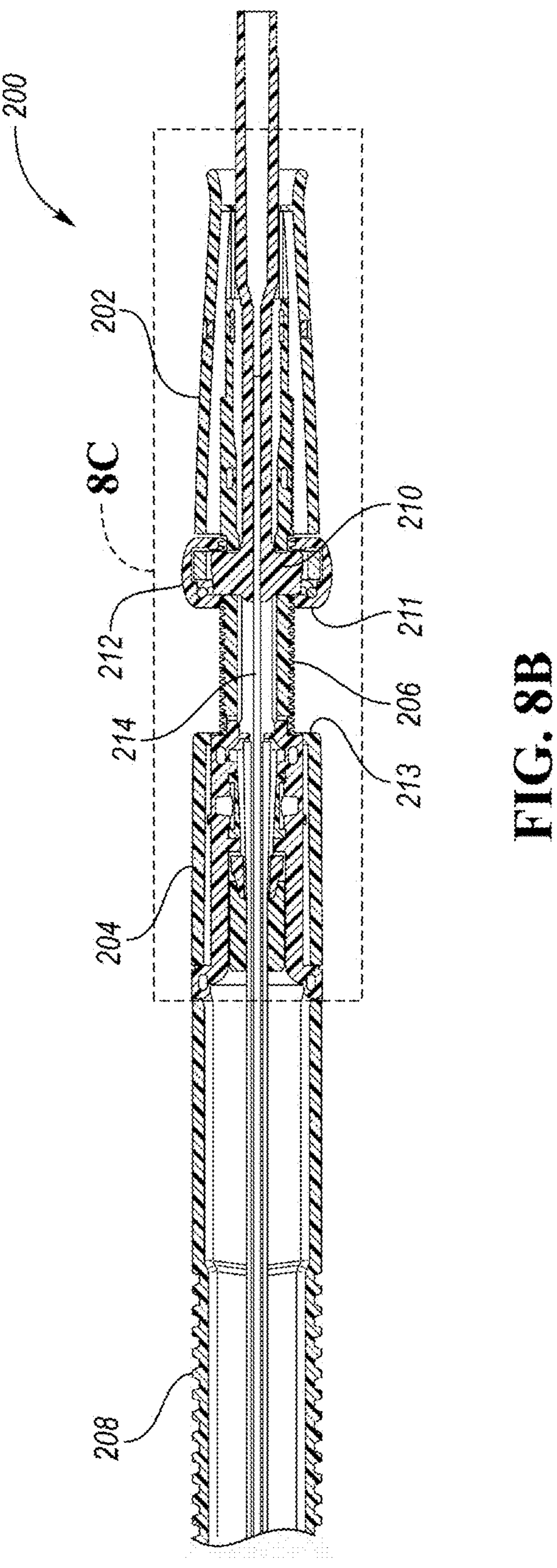
FIG. 8B is a cross-sectional view taken along line 8B-8B of FIG. 8A.
Figure 8C:
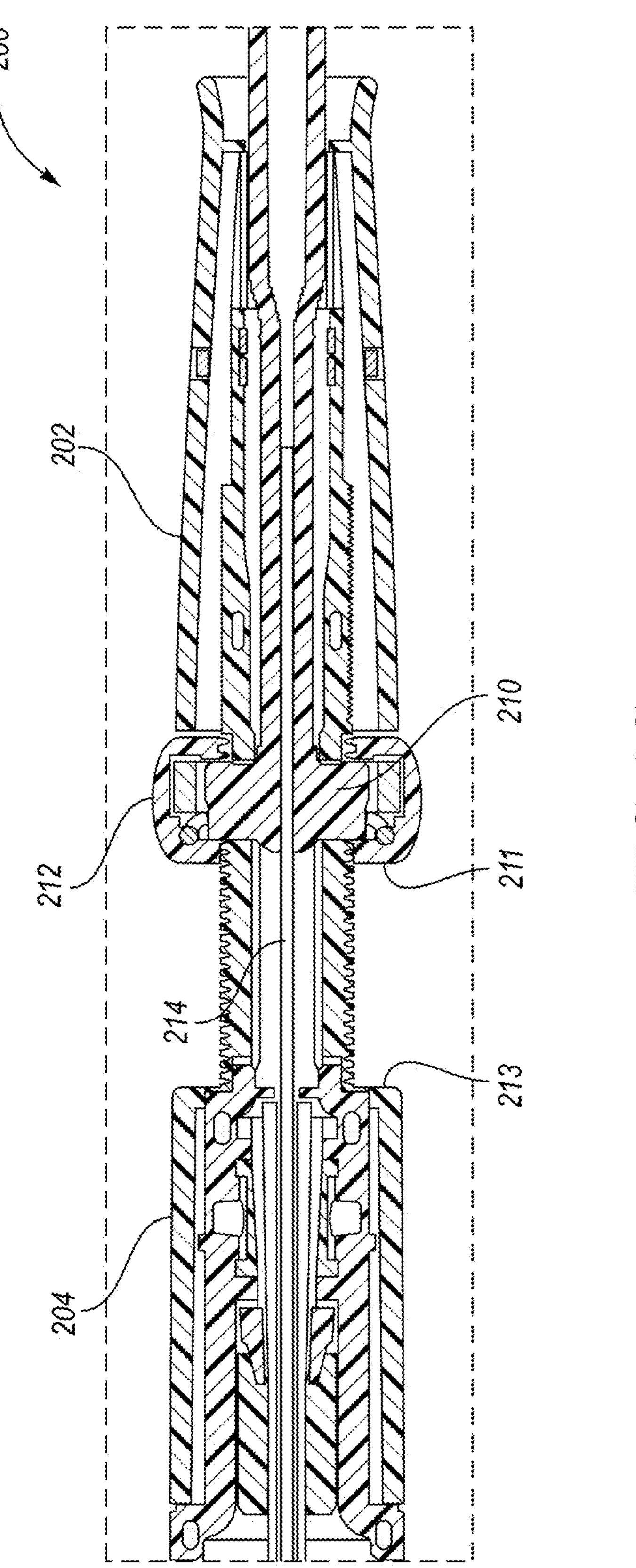
FIG. 8C is a magnified, cross-sectional view of FIG. 8B.
Figure 9A:
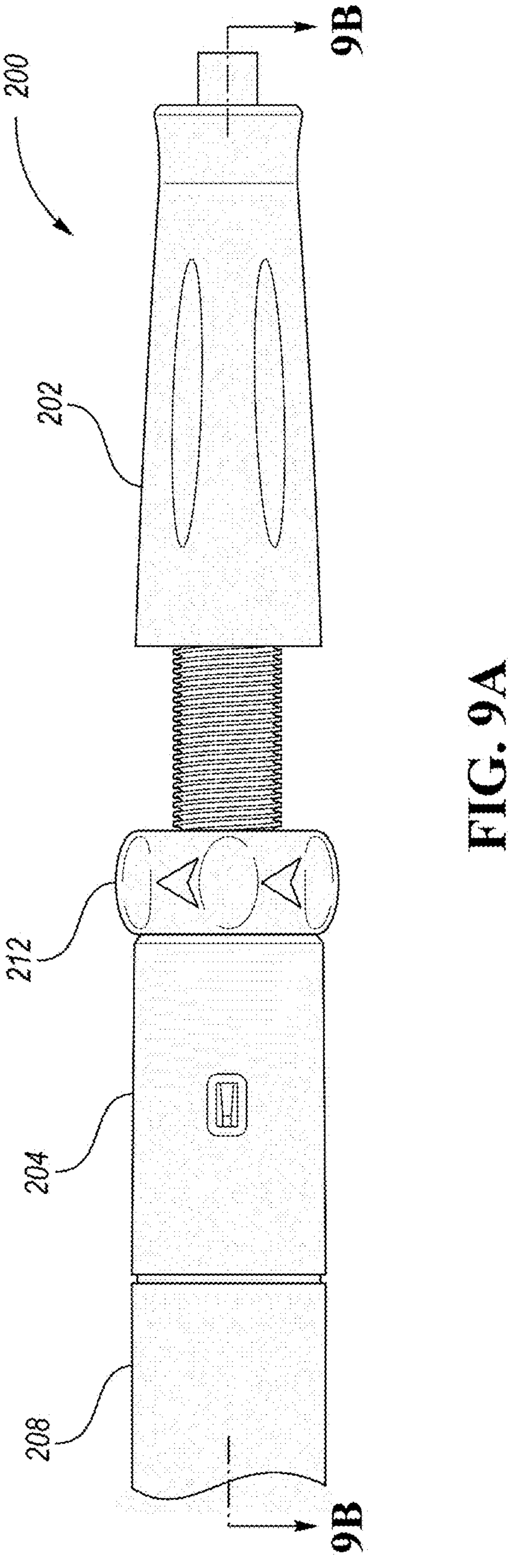
FIG. 9A is a fragmented, side view of the handle assembly of FIG. 8A in a release position.
Figure 9B:
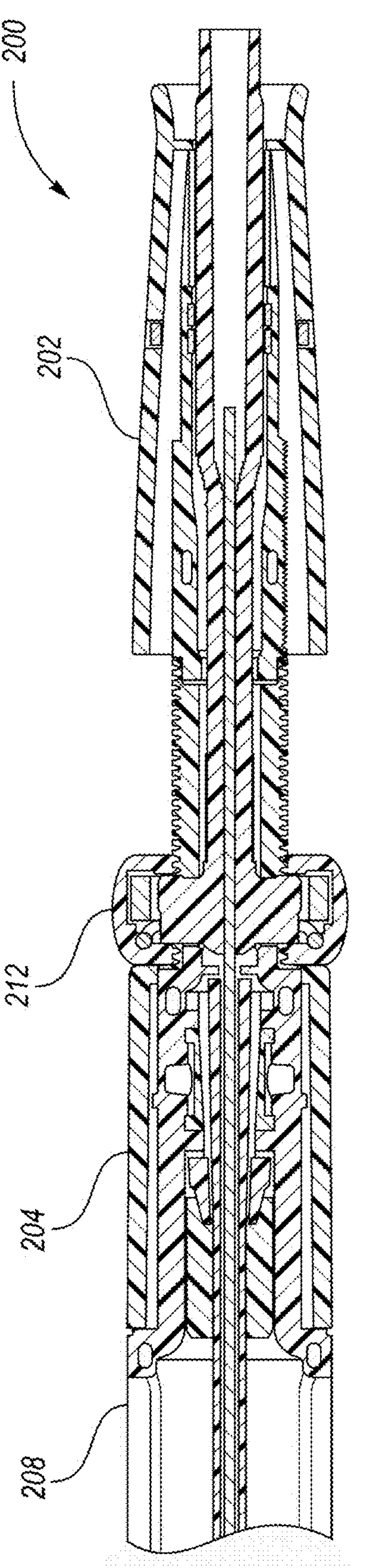
FIG. 9B is a cross-sectional view taken along line 9B-9B of FIG. 9A.

As shown in FIG. 8A, the linear gap G between distal end 211 of thumb wheel 212 and proximal end 213 of rear grip 204 is depicted. The linear gap G may be matched with the travel distance T shown in FIG. 3C to position proximal end 112 of sleeve 106 at landing zone 55. In one embodiment, the travel of thumb wheel 212 axially matches in a 1:1 ratio with the distance of travel of tip assembly 103. In other embodiments, the dimensions of the threading of back end thread 206 creates a different ratio. Inner member 214 is coupled to tip assembly 103 and back end T-tube 210, which is coupled to thumb wheel 212, thereby permitting rotational movement of thumb wheel 212 along back end thread 206 to be translated to axial movement of tip assembly 103 through inner member 214 via the T-tube 210. Thumb wheel 212 includes an inner surface with threads complimentary to back end thread 206 such that thumb wheel 212 travels along back end thread 206 through linear gap G. Rotating thumb wheel 212 in the direction of the arrows shown in FIG. 8A advances thumb wheel 212 along back end thread 206 from the delivery position to the advanced position shown in FIGS. 9A and 9B. The advanced rotational movement stops upon thumb wheel 212 contacting proximal end 213 of rear grip 204, thereby stopping tip assembly 103 in the advanced position. The travel of thumb wheel 212 between the delivery position and the advanced position is matched to the travel distance T, thereby positioning sleeve 106 of tip assembly 103 on landing zone 55. While proximal end 213 is configured to stop movement of thumb wheel 212, discontinuation of back end thread 206 into a smooth surface may also be used as a stop. Alternatively, a stop may be placed on back end thread 206.

When thumb wheel 212 stops at proximal end 213 of rear grip 204, then proximal end 112 of sleeve 106 has reached a location where it meshes with the regular contour of landing zone 55 so that an overall profile of delivery system 100 remains smooth and edgeless as possible during withdrawal of delivery system 100, thereby reducing or minimizing any impact of the sharp features of proximal end 112 of sleeve 106. The positioning of sleeve 106 over landing zone 55 is resistant to inadvertent slippage because only rotational movement of thumb wheel 212 in a retracted direction changes the position in one direction and proximal end 213 of rear grip 204 precludes movement in the other direction.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, case of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A delivery system for delivering an endovascular graft within a blood vessel, the delivery system comprising:

a tip assembly including a tip and a sleeve having an inner surface; and a tip capture mechanism, the tip assembly configured to move axially relative to the tip capture mechanism and between a delivery position and a release position, the tip capture mechanism includes a cylindrical outer surface and knobs arranged around the cylindrical outer surface, the cylindrical outer surface extends along a longitudinal axis of the tip capture mechanism, each knob has a pyramidal structure with a rounded apex and a base having base edges, contacting portion(s) of the base edges of adjacent knobs contact each other, the contacting portion(s) align along the longitudinal axis, and the knobs and inner surface of the sleeve configured to cooperate to hold a portion of the endovascular graft when the tip capture mechanism and the tip assembly are in the delivery position.

2. The delivery system of claim 1, wherein the pyramidal structure of each knob has rounded lateral edges.

3. The delivery system of claim 1, wherein the pyramidal structure of each knob has rounded base edges.

4. The delivery system of claim 1, wherein the cylindrical outer surface is an elongated cylindrical outer surface.

5. The delivery system of claim 4, wherein the knobs are arranged around a circular portion of the elongated cylindrical outer surface normal to the longitudinal axis.

6. The delivery system of claim 5, wherein the knobs are circumferentially, equally spaced around the circular portion.

7. The delivery system of claim 1, wherein the knobs are limited to smooth features with angles that are less than or equal to 45 degrees.

8. The delivery system of claim 1, wherein the tip capture mechanism includes a proximal end and a distal end, the proximal end having a proximal end portion with a proximal end portion diameter, the distal end having a distal end portion with a distal end portion diameter, and the distal end portion diameter is greater than the proximal end portion diameter.

9. A delivery system for delivering an endovascular graft within a blood vessel, the delivery system comprising:

a tip assembly including a tip and a sleeve having an inner surface; and a tip capture mechanism, the tip assembly configured to move axially relative to the tip capture mechanism and between a delivery position and a release position, the tip capture mechanism includes a cylindrical outer surface including a proximal end and a distal end and knobs arranged around the cylindrical outer surface, each knob has a pyramidal structure with a rounded apex and a base having base edges, the base edges of the knobs and the proximal end and the distal end of the cylindrical outer surface bound smooth regions of the cylindrical outer surface, the smooth regions of the cylindrical outer surface are triangular shaped, and the knobs and inner surface of the sleeve configured to cooperate to hold a portion of the endovascular graft when the tip capture mechanism and the tip assembly are in the delivery position.

10. The delivery system of claim 9, wherein the cylindrical outer surface is an elongated cylindrical outer surface extending along a longitudinal axis of the tip capture mechanism.

11. The delivery system of claim 10, wherein the knobs are circumferentially, equally spaced around the elongated cylindrical outer surface.

12. The delivery system of claim 10, wherein the knobs continuously extend around the elongated cylindrical outer surface.

13. The delivery system of claim 9, wherein the knobs are limited to smooth features with angles that are less than or equal to 45 degrees.

14. A delivery system for delivering an endovascular graft within a blood vessel, the delivery system comprising:

a tip assembly including a tip and a sleeve having an inner surface;

a tip capture mechanism, the tip assembly configured to move axially relative to the tip capture mechanism and between a delivery position and a release position, the tip capture mechanism includes a cylindrical outer surface including a proximal end and a distal end and knobs arranged around the cylindrical outer surface, each knob has a pyramidal structure with a rounded apex and a base having base edges, the base edges of the knobs and the proximal end and the distal end of the cylindrical outer surface bound smooth regions of the cylindrical outer surface, the smooth regions include proximal end bordered smooth regions and distal end bordered smooth regions spaced apart from the proximal end bordered smooth regions, and the knobs and inner surface of the sleeve configured to hold a portion of the endovascular graft when the tip capture mechanism and the tip assembly are in the delivery position.

* * * * *